(12) United States Patent
Harosh

(10) Patent No.: US 6,942,967 B1
(45) Date of Patent: *Sep. 13, 2005

(54) TARGET FOR TREATING ATHERSCLEROSIS, OBESITY AND TYPE II DIABETES

(75) Inventor: Itzik Harosh, Paris (FR)

(73) Assignee: Obe Therapy Biotechnology, Evry (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/607,437

(22) Filed: Jun. 29, 2000

Related U.S. Application Data

(63) Continuation of application No. PCT/FR98/02883, filed on Dec. 28, 1998.

(30) Foreign Application Priority Data

Dec. 30, 1997 (FR) .......................................... 97 16655

(51) Int. Cl.$^7$ ................................................. C12Q 1/68
(52) U.S. Cl. ........................ 435/6; 435/91.1; 536/22.1; 536/23.1
(58) Field of Search ........................ 514/44; 536/24.5, 536/22.1, 23.1; 435/6, 91.1

(56) References Cited

U.S. PATENT DOCUMENTS 6,210,888 B1 * 4/2001 Harosh

FOREIGN PATENT DOCUMENTS

| FR | 2 762 014 | 10/1998 |
|---|---|---|
| WO | WO 98/45472 | 10/1998 |

OTHER PUBLICATIONS

Kenney et al. Blood 92(5):1721–127; 1998 "Antisense to the epstein–barr virus (EBV)–encoded latent membrane protein 1 (LMP–1) suppresses LMP–1 and bcl–2 expression and promotes apoptosis in EBV–immortalized B cells."*

Teng et al. Scecience 1993 (260):1816–1819 "Molecular cloning of an ApolipoproteinB messenger RNA editing protein".*

Farnier M. et al. Current and future treatment of hyperlipidemia: the role of statins. American Journal of Cardiology, vol. 82, No. 4B, pp. 3J–10J; 1998.*

Knowles et al. Genetic modifiers of atheroslerosis in mice. Artioscler. Thromb. Vasc. Biol., vol. 20, No. 11, pp. 2336–2345; 2000.* van Tilburg J. et al. Defining the genetic contribution of type 2 diabetes mellitus. Journal of Medical Genetics, vol. 38, No. 9, pp. 569–578; 2001.*

Braasch, D. et al. Biochemistry 2002; vol. 41, No. 14, pp. 4503–4510.*

Branch, A. Trends in Biochemistry 1998; vol. 23, pp. 45–50.*

Gewirtz, A. et al. Proc. Natl. Acad. Sci., U.S.A. 1996; vol. 93, pp. 3161–3163.*

Agrawal, S. Trends in Biotechnology 1996, vol. 14, pp. 376–387.*

Tamm, I. et al. The Lancet 2001, vol. 358, pp. 489–497.*

Bostrom. K., "Apolipoprotein B m RNA Editing". *The Journal of Biological Chemistry*. vol. 265, No. 36, pp. 22446–22452 (1990).

Patel S., "Chylomicron retention disease: exclusion of apolipoprotein B gene defects and detection of mRNA editing in an affected family". *Atherosclerosis*. vol. 108, pp. 201–207 (1994).

GenBank Accession No. D90151, May 25, 1990.
GenBank Accession No. L26234, Jan. 4, 1995.
GenBank Accession No. U76713, Oct. 30, 1996).
GenBank Accession No. U22264, Mar. 6, 1995.
GenBank Accession No. L07114, Apr. 4, 1994.
GenBank Accession No. U10695, Jun. 14, 1994.

Lau, et al.; "Cloning of an Apobec–1–binding Protein That Also Interacts with Apolopoprotein B mRNA and Evidence for Its Involvement in RNA Editing"; *Journal of biological Chemistry*; Jan. 17, 1997; vol. 272, No. 3, pp. 1452–1455.

Phung, et al.: "Regulation of Hepatic Apolipoprotein B RNA Editing in the Genetically Obese Zucker Rat"; *Metabolism*; Sep. 1996; vol. 45, pp. 1056–1058.

Oka, et al.: "Tissue–specific Inhibition of Apolipoprotein B mRNA Editing in the Liver by Adenovirus–mediated Transfer of a Dominant Negative Mutant APOBEC–1 Leads to Increased Low Density Lipoprotein in Mice"; *Journal of Biological Chemistry*; Jan. 17, 1997; vol. 272, pp. 1456–1460.

Anant, et al, "AU–rich RNA Binding proteins Hel–N1 and AUF1 bind apolipoprotein B mRNA and inhibit posttranscriptional C to U editing"; *Nucleic Acids Symposium Series*; 1997; vol. 36, pp. 115–118.

Greeve, et al.: "Reconstitution of apoB mRNA editing in liver by gene–transfer as a potential approach for the treatment of severe forms of polygenic hypercholesterolemia–an outline of the rationale"; *Zeitschrift Fuer Gastroenterologie*; Jun. 1996; vol. 34, No. Suppl. 03, pp. 27–30.

(Continued)

Primary Examiner—Dave T. Nguyen
Assistant Examiner—Jon Eric Angell
(74) Attorney, Agent, or Firm—Merchant & Gould P.C.

(57) ABSTRACT

The invention concerns the use of the apobec-1 protein or associated proteins for treating atherosclerosis and obesity, type II diabetes (non-insulin-dependent), or other diseases, characterised in particular by hyperlipidemia and/or hyperglycemia, caused for example by a level of chylomicrons and/or VLDL in the plasma above normal. The invention also concerns the cloning of the gene(s) of Anderson disease as target for treating atheroscelerosis, obesity and type II diabetes (non-insulin-dependent), or other diseases characterised in particular by hyperlipidemia and/or hyperglycermia.

10 Claims, 4 Drawing Sheets

OTHER PUBLICATIONS

Smith, et al.: "Base–modificaton mRNA editing through deamination—the good, the bad and the unregulated"; *Trends in Genetics*; Oct. 1996; vol. 12, No. 10, pp. 418424.

Chan I. (1995) "Apolipoprotein B messenger RNA editing; An update"Biochimie. pp. 75–78.

Teng B et al. (1993) "Molecular cloning of an Apolipoprotein B Messenger RNA Editing Protein" Science, vol. 260, pp. 1816–1819.

Lau PP (1994) "Dimeric structure of a human apolipoprotein B mRNA editing protein and cloning and chromosomal localization of its gene" Proc. Natl. Acad. Sci. USA. vol. 91, pp. 8522–8526.

Giannoni et al (1994) "Complementation of Apolipoprotein B mRNA Editing by Human Liver Accompanied by Secretion of Apolipoprotein B48" J. Biol. Chem., vol. 269, No. 8, pp. 5932–5936.

Hirano K et al. (1996) "Targeted Disruption of the mouse apobec–I Gene Abolishes Apolipoprotein B mRNA Editing and Eliminates Apolipoprotein B48" A. Biol. Chem., vol. 271, pp. 9887–9890.

Morrison JR et al (1996) "Apolipoprotein B RNA editing enzyme deficient mice are viable despite alterations in lipoprotein metabolism," Proc. Natl. Acad. Sci. USA, vol. 93, pp. 7154–7159.

Havel RJ and Kane JP (1995) "The metabolic and molecular basis of inherited disease", Chapter 56 and Chapter 57. pp 1841–1885.

Sharp D et al. (1993) "Cloning and gene defects in microsomal triglyceride transfer protein associated with abetalipoproteinaemia" Nature, vol. 365, pp. 65–69.

Wetterau JR et at. (1992) "Absence of Microsomal Triglyceride Transfer Protein in Individuals with Abetalipoproteinemia" Science, vol. 258, pp. 999–1001.

Linton MF et al. (1993) "Familial hypobetalipoproteinemia" J Lipid res., vol. 34, pp. 521–541.

Rosseneu M and Lauber CL (1995)"Physiological significance of apolipoprotein mutants" FASEB J., pp. 768–776.

Anderson CM et al. (1961) "Unusual Causes of steatorrhoea in infancy and childhood". Med. J. Aust., pp. 617–622.

Pessah M et al. (1991) "Anderson's Disease: Genetic Exclusion of the Apolipoprotein–B Gene in Two Families" J. din. Invest., vol. 87, pp. 367–370.

Strich D et al. (1993) "Anderson's Disease: No linkage to the apo B Locus" J. Pediatric Gastro. Nutrit., vol. 16, No. 3, pp. 257–264.

Levy E et al. (1987) "Intestinal apoB synthesis, lipids, and lipoproteins in chylomicron retention disease" J. Lipid Res., vol. 28, pp. 1263–1274.

Shah RR et al. (1991) "Sequence Requirements for the Editing of Apolipoprotein B mRNA" J. Biol. Chem., vol. 266, No. 25, pp. 16301–16304.

Kaneko–Ishino T et al., (1995) "Peg1/Mest imprinted gene on chromosome 6 identified by cDNA subtraction hybridization", Nature Genet., vol. 11, pp 52–59.

Davies MS et al (1989) "Sequence Requirements for Apolipoprotein B RNA Editing in Transfected Rat Hepatoma Cells". J Biol Chem. vol. 264, No. 23, pp. 13395–13398.

Uhlmann P and Peyman A (1990)"Antisense Oligonucleotides A New Therapeutic Principle" Chem Rev. vol. 90, No. 4, pp. 543–584.

Bostrom, K., "Apolipoprotein B m RNA Editing", *The Journal of Biological Chemistry*, vol. 265, no. 36, pp. 22446–22452 (1990).

Patel, S., "Chylomicron retention disease: exclusion of apolipoprotein B gene defects and detection of mRNA editing in an affected family", *Atherosclerosis*, vol. 108, pp. 201–207 (1994).

Barroso et al., "Dominant negative mutations in human PPARγ associated with severe insulin resistance, diabetes mellitus and hypertension", *Nature*, 402:880–883 (Dec. 1999).

Harris et al., "RNA Editing Enzyme APOBEC1 and Some of its Homologs can Act as DNA Mutators", *Mol. Cell*, 10:1247–1253 (Nov. 2002).

Kendrick et al., "Superior role of apolipoprotein B48 over apolipoprotein B100 in chylomicron assembly and fat absorption: an investigation of apobec–1 knock–out and wild–type mice", *Biochem. J.*, 356:821–827 (2001).

Larsen et al., "PPARgamma agonists in the treatment of type II diabetes: is increased fatness commensurate with long–term efficacy", International Journal of Obesity, 27:147–161 (2003).

Taboit–Damcron et al., "Association of the 5'HS4 sequence of the chicken β–globin locus control region with human EF1αgene promoter induces ubiquitous and high expression of human CD55 and CD59 cDNAs in transgenic rabbits", *Transgenic Res.*, 8:223–235 (1999).

Teng et al., "Adenovirus–mediated Gene Transfer of Rat Apoloipoprotein B mRNA–editing Protein in Mice Virtually Eliminates Apolipoprotein B–100 and Normal Low Density Lipoprotein Production", *J. Biol. Chem.*, 269(47):29395–29404 (1994).

* cited by examiner

TARGET FOR TREATING ATHERSCLEROSIS, OBESITY AND TYPE II DIABETES

This application is a continuation of and claims the benefit of, international application number PCT/FR98/02883, filed 28 Dec. 1998, which claims the benefit of French Patent Application No. 97/16655, filed 30 Dec. 1997.

This invention relates to apobec-1 enzyme and the associated proteins which enable the production of the protein apoB48 in the intestine. The invention is especially applicable to a method for detecting inhibitors of apobec-1 and associated proteins, and to the use of the gene(s) for Anderson's disease as a target for a treatment for atherosclerosis, obesity, type II diabetes (non-insulin dependent) or other diseases characterized in particular by a higher than normal level of chylomicrons and/or VLDL in the plasma (hyperlipidemia, such as hypercholesterolemia, hyperglyceridemia, etc) and/or by hyperglycemia.

The apoB gene codes for two proteins, apoB100 and apoB48. These two proteins are translated by the same messenger RNA, modified at a single nucleotide by a specialized enzyme, apobec-1 (apoB editing compound 1) and associated proteins. In the human digestive system, this enzyme is expressed in the intestine but not in the liver. In the intestine, it modifies codon 6666 of the apoB messenger RNA by creating a stop codon which results in the production of a polypeptide known as apoB48 (48% of messenger RNA translated). ApoB48 is essential for the formation of chylomicrons which act to absorb and transport cholesterol, triglycerides and other lipids originating in the intestine. In the liver, where the apobec-1 enzyme is not expressed, and where no modification of the apoB messenger RNA takes place, the protein produced is apoB100, belonging to the very low density lipoproteins (VLDL) and low density lipoproteins (LDL) families.

Currently, three human genetic diseases exist which affect the level of apoB expression, all with similar phenotypes: abetalipoproteinemia, hypobetalipoproteinemia and Anderson's disease, also known as chylomicron retention disease. Abetalipoproteinemia is due to a deficiency of MTP (microsomal transfer protein) while hypobetalipoproteinemia is due to multiple mutations of the apoB gene. In those two cases, neither VLDL nor chylomicrons can be detected in the plasma, respectively associated with the absence of apoB100 and apoB48.

In contrast, in Anderson's disease, only chylomicrons (apoB48) are lacking in the plasma, while VLDLs (apoB100) remain detectable.

In this invention, it is suggested:
1. that the apobec-1 enzyme and its associated proteins are potential targets for the treatment of atherosclerosis and obesity, and other diseases principally characterized by a higher than normal level of chylomicrons and/or VLDL in the plasma (hyperlipidemia, such as hypercholesterolemia, hypertriglyceridemia, etc) and/or by hyperglycemia;
2. that the gene(s) responsible for Anderson's disease are potential targets for the treatment of atherosclerosis and obesity, and other diseases principally characterized by a higher than normal level of chylomicrons and/or VLDL in the plasma (hyperlipidemia, such as hypercholesterolemia, hypertriglyceridemia, etc) and/or by hyperglycemia;
3. that the apobec-1 gene or the genes coding for the associated proteins are candidate genes for Anderson's disease.

Human apoB protein is the principal apolipoprotein of triglyceride-rich lipoproteins (present in VLDL, LDL and chylomicrons). Its gene is expressed both in the intestine and in the liver. The liver produces a 4536 amino acid protein known as apoB100, while in the intestine, the same gene codes for a smaller protein containing 2152 amino acids, known as apoB48. This protein is identical to the N-terminal portion of apoB100. ApoB48 is the result of translation of apob messenger RNA (mRNA) modified post-transcriptionally by the apobec-1 enzyme (editing protein of apoB messenger RNA) at nucleotide 6666 (cytidine), which undergoes deamination to uridine. This modification of apoB messenger RNA creates a stop codon (UAA) (see FIG. 1 and Chan L (1995), Biochimie 75–78).

In humans and rats, the complementary DNA (cDNA) which codes for apobec-1 has recently been cloned and sequenced (Teng B et al (1993), Science, 1816–1819, Lau P P (1994), Proc. Natl. Acad. Sci. USA 8522–8526). In man, this gene is only expressed in the small intestine, the only location where apoB48 and chylomicrons are produced. In the human liver, no apoB48 production takes place, which is concomitant with the absence of observation of the apobec-1 enzyme in that organ. In contrast, in the rat, where apoB100 and apoB48 are produced in the liver and in the intestine, apobec-1 is expressed in both organs, suggesting an essential role for this protein in the production of apoB48 (Giannoni et al (1994) J. Biol. Chem., 5932–5936). Further, the same authors have demonstrated that transfection of HepG2 hepatic cells with an apobec-1 cDNA leads to a modification of endogenous apoB mRNA, and to secretion of apoB48 protein (Giannoni et al (1994) J. Biol. Chem., 5932–5936).

Finally, it has recently been demonstrated that transgenic mice which are knock-out for the apobec-1 gene lose apobec-1 activity and have no trace of apoB48 in the blood circulation (Hirano K I et al (1996), J. Biol. Chem. 7154–7159, Morrison J R et al (1996), Proc. Natl. Acad. Sci. USA, 9887–9890).

Three human diseases of genetic origin with a similar phenotype have been described: abetalipoproteinemia, hypobetalipoproteinemia and Anderson's disease, also known as chylomicron retention disease (Table 1 and Havel R J and Kane J B (1995), in "The metabolic and molecular basis of inherited disease"). The genetic cause of two of these diseases, abetalipoproteinemia and hypobetalipoproteinemia, has been elucidated. In the case of abetalipoproteinemia, a frameshift mutation has been described in the gene for the MTP (microsomal triglyceride transfer) protein which leads to a complete absence of this protein and its activity. As a result, this mutation prevents the formation and secretion of lipoproteins containing apoB and thus prevents the detection of apoB100 and apoB48 in the plasma of patients (Sharp D et al (1993), Nature, 65–69, Wetterau J R et al (1992), Science, 999–1001). Hypobetalipoproteinemia is a disease in which different mutations of the apoB gene have been described, leading to truncated apoB proteins of different sizes. At the present time, 25 different mutations (nonsense or frameshift) have been described as being at the origin of hypobetalipoproteinemia, resulting in a premature stop codon (Linton M F et al (1993), J. Lipid. Res., 521–541, Rosseneu M and Lauber C (1995), FASEB J., 768–776). The mechanisms by which these truncations of the apoB protein lead to hypobetalipoproteinemia are as yet unknown. In the case of abetalipoproteinemia and hypobetalipoproteinemia, the absence of chylomicron absorptions also leads to an absence of vitamin E absorption, creating severe neurological symptoms.

The third of these genetic diseases with similar phenotypes, chylomicron retention disease, first described by Anderson 36 years ago (Anderson C M et al (1961), Med. J. Aust., 617–621) is still an enigma. This disease is characterized by chronic diarrhoea, deficient fat absorption and a lack of energy. In certain cases, neurological symptoms due to an absence of vitamin E are observed, but these are less severe than in the case of abetalipoproteinemia and hypobetalipoproteinemia (Havel R J and Kane J B (1995) in "The metabolic and molecular basis of inherited disease"). These diseases appear to be inherited in a recessive autosomal manner. Finally, analysis of the plasma of patients shows a total absence of chylomicrons and apoB48 protein (Havel R J and Kane J B (1995) in "The metabolic and molecular basis of inherited disease").

Genetic linkage studies using RFLP (restriction fragment length polymorphism) have shown that the apoB gene is not involved in Anderson's disease (Pessah M et al (1991), J. Clin. Invest. 367–370, Stritch et al (1993), J. Pediatric Gastro. Nutrit., 257–264). In patients with Anderson's disease, MTP activity is normal, which suggests that a different gene is implicated in this disease (Linton M F et al (1993), J. Lipid Res., 521–541). These and other experiments thus suggest that the origin of Anderson's disease is not linked with secretion via MTP and that chylomicron retention involves a further mechanism (Wetterau J R (1992), Science, 999–1001).

The present invention proposes that the gene for the apobec-1 protein is a candidate for Anderson's disease for the following reasons:

1. apobec-1 is exclusively expressed in the intestine;
2. apoB48 and chylomicrons are absent in the plasma of patients with Anderson's disease, while VLDL containing apoB100 are present. This constitutes the principal phenotype of patients with Anderson's disease;
3. mice which are knock-out for the apobec-1 gene lose apobec-1 activity and the mRNA modification which ordinarily leads to the apoB48 protein, leading to the absence of this protein in the plasma (Hirano K I et al (1996) J. Biol. Chem. 7154–7159, Morrison J R et al (1996), Proc. Natl. Acad. Sci. USA 9887–9890);
4. the apobec-1 activity of obese Zucker rats is 42% higher than that of non obese control rats, with the result that the level of chylomicrons and apoB48 in the blood is 4.7 times higher than that of the control rats (Phung T L et al (1996), Metabolism, 1056–1058);
5. it has also been proposed that Anderson's disease is due to a modification in other genes involved in the protein secretion or glycosylation route (Levy E et al (1987), J. Lipid. Res., 1263–1274). Their results clearly show that one patient with Anderson's disease out of the three patients studied had a high level of apoB100 and relatively little apoB48. Using a more sensitive detection system, radioactive labelling followed by a SDS-PAGE analysis, for example, a visible amount of apoB100 was detected in the other two patients. The probable presence of apoB48 among the other visible bands of proteins which are smaller than apoB100 could be explained by degradation of apoB100.

Finally, it has been demonstrated that a mutation in the anchoring sequence around the apoB mRNA deamination site (site 6666) can cause a reduction or even a loss in editing of this site (Shah R R et al (1991), J. Biol. Chem., 16301–16304). It is thus not excluded that Anderson's disease is a particular case of hypobetalipoproteinemia wherein certain mutations of the apoB100 gene uniquely affect the formation and secretion of chylomicrons, while the formation and secretion of VLDL are not affected.

Thus the present invention suggests that a mutation or other modification of the anchoring sequence around the apoB mRNA deamination site may be at the origin of Anderson's disease.

In order to test the hypothesis that the apoB gene is a candidate for Anderson's disease, the present invention proposes to use RT-PCR (reverse transcriptase polymerase chain reaction) to sequence the apoB mRNA of intestinal biopsies of patients suffering from Anderson's disease, around the anchoring sequence surrounding site 6666, and to study the degree of deamination (C→U conversion) of this site. If no modification or mutation of the anchoring sequence surrounding the deamination site is observed, this will be highly indicative that the origin of Anderson's disease is due to apobec-1 or the associated proteins.

To test the hypothesis that the apobec-1 protein gene is at the origin of Anderson's disease, the present invention proposes to re-clone and sequence the apobec-1 gene in the patients. To test the hypothesis that the gene for the ABBP-1 gene (apobec-1 binding protein), the only protein associated with apobec-1 which has been cloned at present (Lau P P et al (1997), J. Biol. Chem., 1452–1455), is at the origin of Anderson's disease, the present invention proposes to re-clone and sequence the ABBP-1 gene in patients, to detect any differences with the normal genotype. In the case where other proteins associated with apobec-1 should be cloned, the present invention proposes to adopt the same technique to test the hypothesis that those are at the origin of Anderson's disease.

In the case where Anderson's disease is not due to modification of the apoB sequence, nor to modification of the apobec-1 protein and its associated proteins which are known and cloned, the present invention proposes to clone the responsible gene(s) by a subtractive hybridization technique as described in Example 1 (Kaneko-Ishino T (1995), Nature. Genet., 52–59) or a cloning technique by detecting point mutations using mutS protein as described in Example 2.

This invention also concerns apobec-1 inhibitor molecules or associated proteins for therapeutic use in the case of atherosclerosis or obesity, and other diseases characterized by a higher than normal level of chylomicrons and/or VLDL in the plasma (hyperlipidemia, such as hypercholesterolemia, hypertriglyceridemia, etc) and/or by hyperglycemia, obtained using a technique for detecting deamination of a cytidine in an RNA (French patent application 97 04388) as described in Example 3. The deaminated cytidine studied here is the cytidine in position 6666 of the apoB mRNA, the RNA sequence used as a substrate containing the apobec-1 anchoring zone or associated proteins is as described in the literature (Shah R R et al (1991), J. Biol. Chem., 16301–16304, Davies M S et al (1989), J. Biol. Chem., 13395–13398), and the protein extracts used can originate from the rat liver or from other sources. The sequence used as a primer in carrying out the technique contains a number of complementary nucleotides of the 3' sequence of site 6666 of the apoB mRNA sufficient for correct hybridization (14 nucleotides or more).

Thus the present invention concerns the use of the gene for the apobec-1 enzyme or the gene for the ABBP-1 protein or that of a protein associated with the apobec-1 enzyme, or a gene involved in Anderson's disease, for research and to producing therapeutic agents or molecules inhibiting expression of one or more of these genes or the activity of enzymes or proteins expressed by these genes.

The present invention also concerns the use of therapeutic agents or molecules discovered and produced in accordance with the preceding claim for the prevention, stabilisation or treatment of atherosclerosis, obesity, type II diabetes (non-insulin dependent), or other diseases characterized by hyperlipidemia, such as hypercholesterolemia, hypertriglyceridemia, etc., and/or by hyperglycemia due, for example, to a higher than normal level of chylomicrons and/or VLDL in the plasma.

The present invention also concerns any therapeutic agent or molecule enabling inhibition of the activity of these enzymes or proteins, or inhibiting expression of these genes.

This invention especially concerns the use of anti-sense nucleic acid molecules which can reduce the quantity of apobec-1 or associated proteins, or the quantity of proteins expressed by the gene(s) for Anderson's disease or any gene involved in the formation, stabilization, secretion, glycosilation or transport of chylomicrons and/or VLDL (Uhlmann E and Peyman A (1990), Chem. Rev., 543–584). Such anti-sense molecules can bind covalently or otherwise to the DNA or RNA of apobec-1 or associated proteins, or to the DNA or RNA of the gene or genes responsible for Anderson's disease or any gene involved in the formation, stabilization, secretion, glycosilation or transport of chylomicrons and/or VLDL. As an example, such an anti-sense molecule linkage can cleave or facilitate cleavage of the DNA or RNA of apobec-1 or associated proteins, or of the gene(s) responsible for Anderson's disease or any gene involved in the formation, stabilization, secretion, glycosilation or transport of chylomicrons and/or VLDL. Such an anti-sense molecule can also increase degradation of the corresponding nuclear or cytoplasmic mRNA, or inhibit its translation, fixing of transcription factors or pre-messenger RNA, or, for example, by inhibiting splicing of pre-messenger RNA. The totality of these modes of anti-sense molecule action have the effect of reducing expression of the apobec-1 gene, or the associated proteins, or of the gene(s) responsible for Anderson's disease or any gene involved in the formation, stabilization, secretion, glycosilation or transport of chylomicrons and/or VLDL, resulting in an important treatment for obesity, type II diabetes (non-insulin dependent) or atherosclerosis, for example.

Non limiting examples of potential targets for such anti-sense molecules which can be cited are sequences of the apobec-1 gene or associated proteins, or the gene(s) responsible for Anderson's disease or any gene involved in the formation, stabilization, secretion, glycosilation or transport of chylomicrons and/or VLDL, but also the 3' and 5' sequences of these genes which could be the control regions for these genes.

The present invention thus also concerns single stranded (DNA or RNA) anti-sense nucleic acid molecules containing at least 12 nucleotides acting on the gene or its RNA, or on a region regulating expression of the gene to inhibit expression of the gene for the apobec-1 enzyme, or of the gene for the ABBP-1 protein, or that of a protein associated with the apobec-1 enzyme, or again a gene involved in Anderson's disease or the activity of the enzymes or proteins expressed by these genes.

BRIEF DESCRIPTION OF THE DRAWINGS

Table 1: Three genetic diseases with similar phenotypes. In the case of abetalipoproteinemia, the MTP has mutated, leading to the absence of particles containing apoB100 or apoB48 in the blood. In the case of hypobetalipoproteinemia, the apoB gene has mutated, resulting in a very low level of VLDL and chylomicrons. Anderson's disease is characterized by the absence of apoB48 alone, resulting in an absence of a detectable level of chylomicrons in the blood.

EXAMPLES

Example 1

Figure 1:
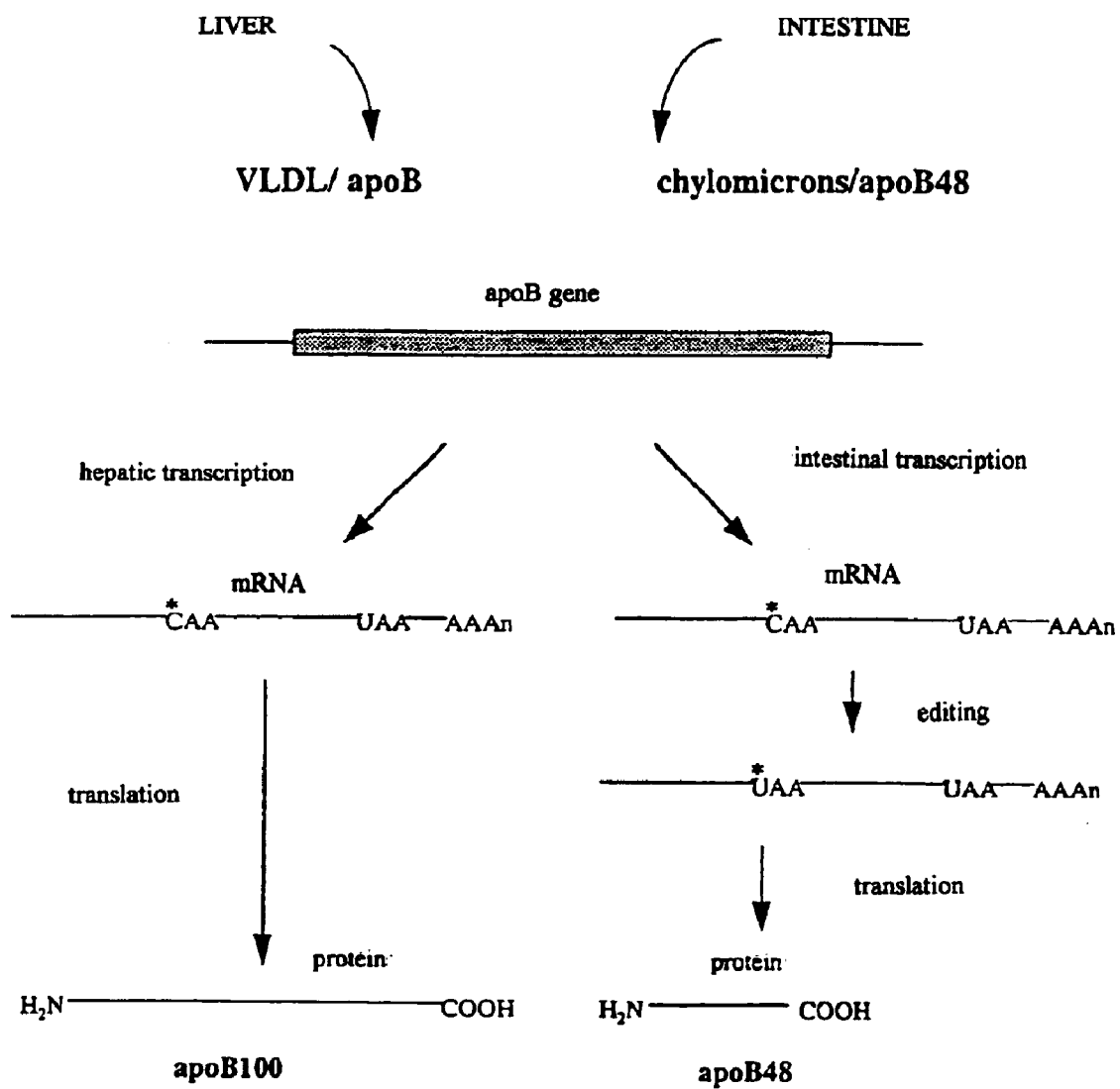
FIG. 1: Expression of apoB. The apoB gene is expressed in the liver and intestine. In the liver, the apoB mRNA is translated into apoB100, while in the intestine, the CAA codon commencing at the position 6666 (indicated by an asterisk) in the mRNA is edited by the apobec-1 enzyme which deaminates the cytidine to uracyl, producing a stop codon resulting in the formation of the apoB48 protein.
Figure 2:
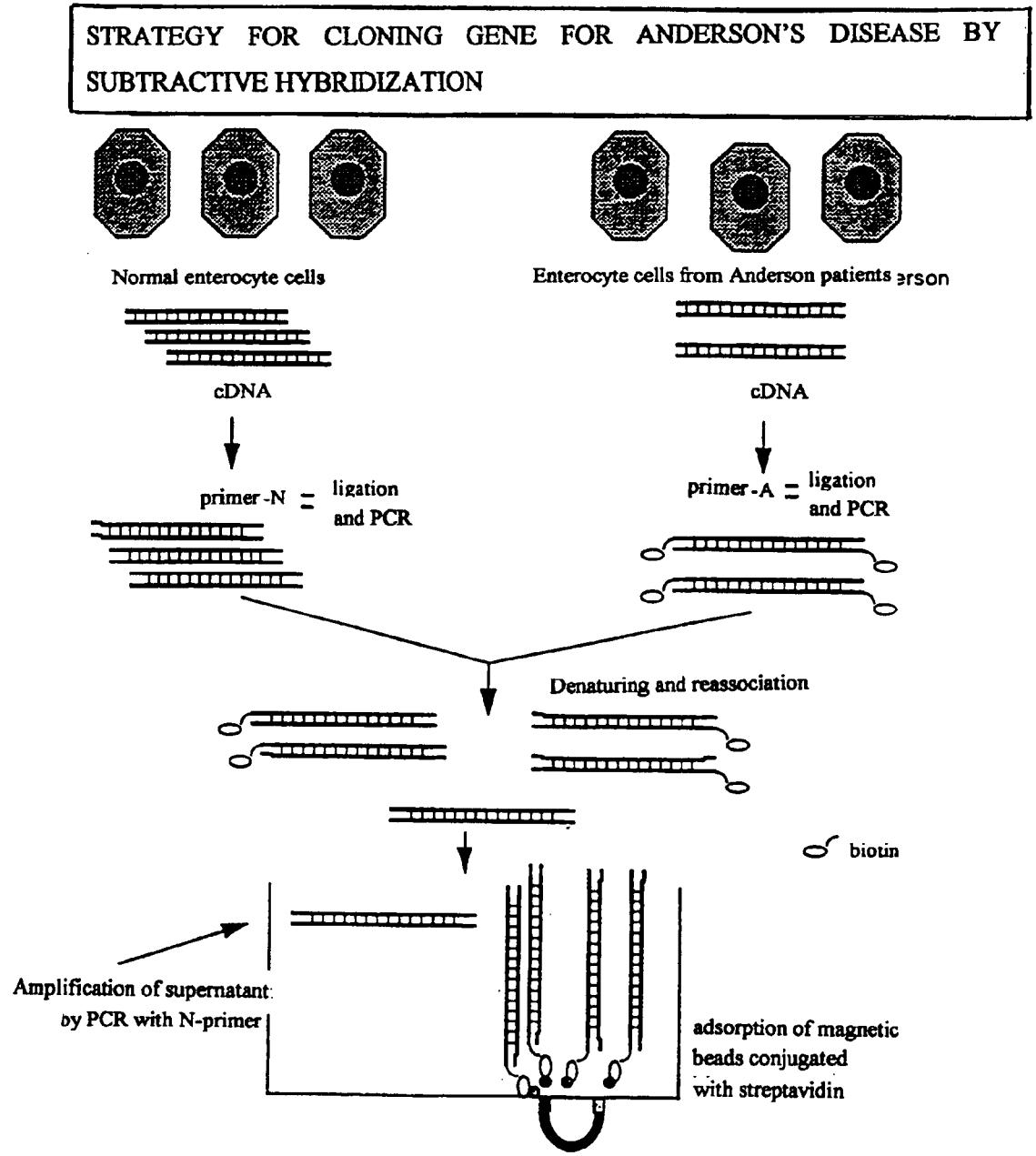
FIG. 2: Cloning of the gene(s) of Anderson's disease by subtractive hybridization. The first step of the technique consists of isolating enterocyte cells from the intestine of a patient and a normal individual. Complementary DNA strands are then produced from the mRNA extracted from these cells, using the reverse transcriptase enzyme. Following synthesis of a second DNA strand complementary to this DNA using DNA polymerase, blunt ends are created. This allows an extension constituted by about twenty base pairs to be ligated at each end. Two different sequences are used for the patient (extension A) and for the normal individual (extension N). The cDNA recovered is amplified by PCR using the sequences corresponding to the two extensions A and N as primers, the primer corresponding to the patient being biotinylated, for example. The modified cDNA of the two individuals is then mixed and placed under denaturing and renaturing (reassociation) conditions. The hybridized cDNA is brought into the presence of magnetic beads coated with streptavidin, to isolate the cDNA of the normal individual corresponding to the non transcribed gene of the patient in solution after repeating several times. This gene is then amplified by PCR using primers corresponding to extension N.

Cloning of the Gene(s) Responsible for Anderson's Disease by Subtractive Hybridization The first step of the example described in FIG. 2 consists of isolating enterocyte cells from the intestine of a patient and a normal individual. Complementary DNA strands are then produced from the mRNA extracted from these cells, using reverse transcriptase enzyme. Following synthesis of a second DNA strand complementary to this DNA using DNA polymerase, blunt ends are created. This allows an extension constituted by about twenty base pairs to be ligated at each end. Two different sequences are used for the patient (extension A) and for the normal individual (extension N). The cDNA recovered is amplified by PCR using the sequences corresponding to the two extensions A and N as primers, the primer corresponding to the patient being biotinylated, for example. The modified cDNA of the two individuals is then mixed and placed under denaturing and reassociation conditions. The hybridized cDNA is brought into the presence of magnetic beads coated with streptavidin, to isolate the cDNA of the normal individual corresponding to the non transcribed gene of the patient in solution after repeating several times. This gene is then amplified by PCR using primers corresponding to extension N.

Example 2

Cloning of the Gene(s) Responsible for Anderson's Disease Using MutS Protein

Figure 3:
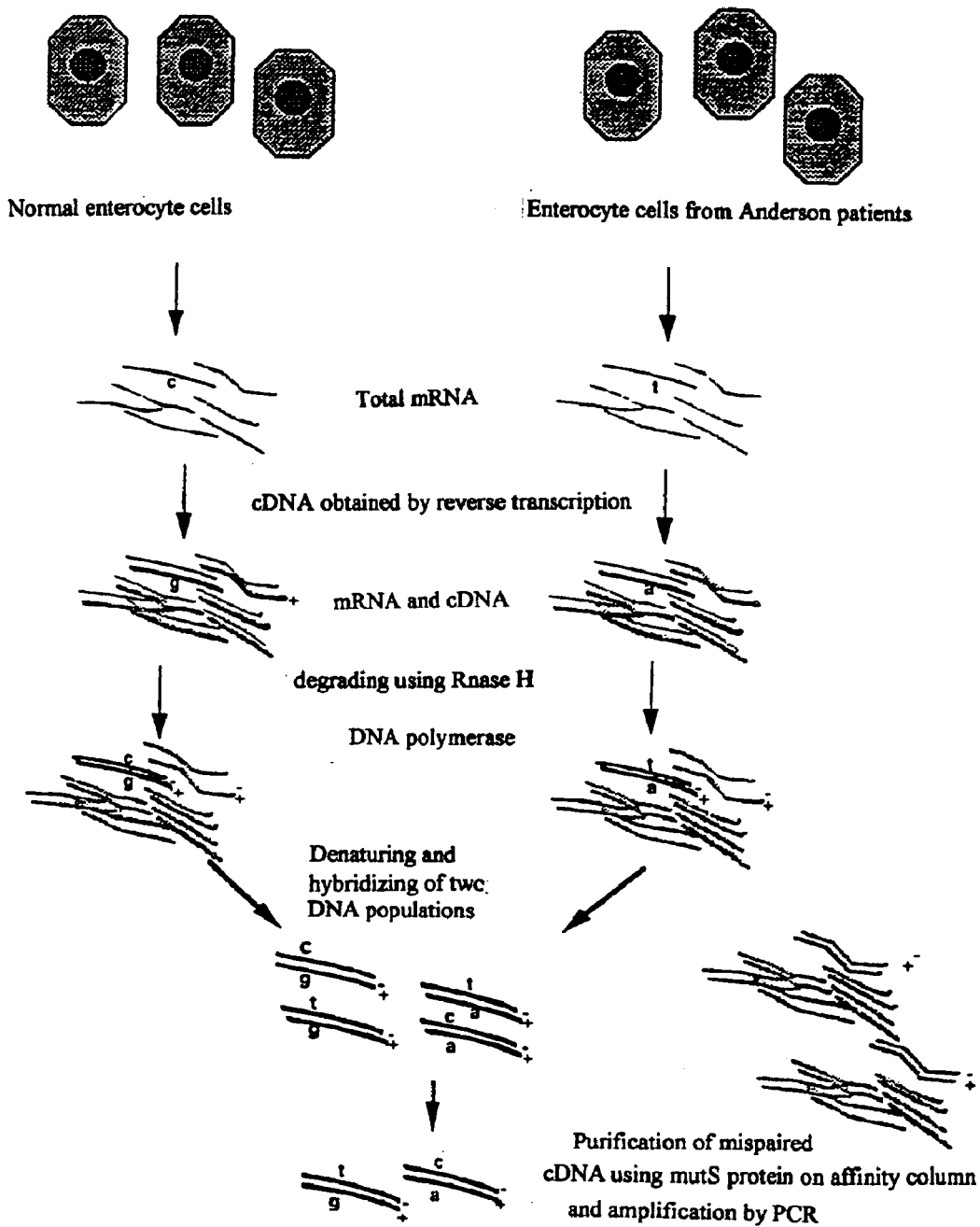
FIG. 3: Cloning of the gene(s) for Anderson's disease using mutS protein. The first step of the technique consists of isolating enterocyte cells from the intestine of a patient and a normal individual. Complementary DNA strands are then produced from the mRNA extracted from these cells in equal amounts for the patient and the normal individual, using the reverse transcriptase enzyme. Following synthesis of a second DNA strand complementary to this DNA using DNA polymerase, blunt ends are created. This allows an extension constituted by about twenty base pairs to be ligated at each end. The modified cDNA of the two individuals is then mixed and placed under denaturing and renaturing (reassociation) conditions. At the moment of hybridization the point mutation in the desired gene does not prevent re-pairing of the two complementary strands despite the mis-pairing of one base pair. The hybridized cDNA is then purified on an affinity column containing immobilized mutS protein. It is then possible to use it to screen a library of intestinal cDNA or total genomic cDNA.

The first step of the example described in FIG. 3 consists of isolating enterocyte cells from the intestine of a patient and a normal individual. Complementary DNA strands are then produced from the mRNA extracted from these cells in equal quantities for the patient and the individual, using reverse transcriptase enzyme. Following synthesis of a second DNA strand complementary to this DNA using DNA polymerase, blunt ends are created. This allows an extension constituted by about twenty base pairs to be ligated at each end. The modified cDNA of the two individuals is then mixed and placed under denaturing and reassociation conditions. At the moment of hybridization the point mutation in the desired gene does not prevent re-pairing of the two complementary strands despite the mis-pairing of one base pair. The hybridized cDNA is then purified on an affinity column containing immobilized mutS protein. It is then possible to use it to screen a library of intestinal or total genomic cDNA.

Example 3

Figure 4:
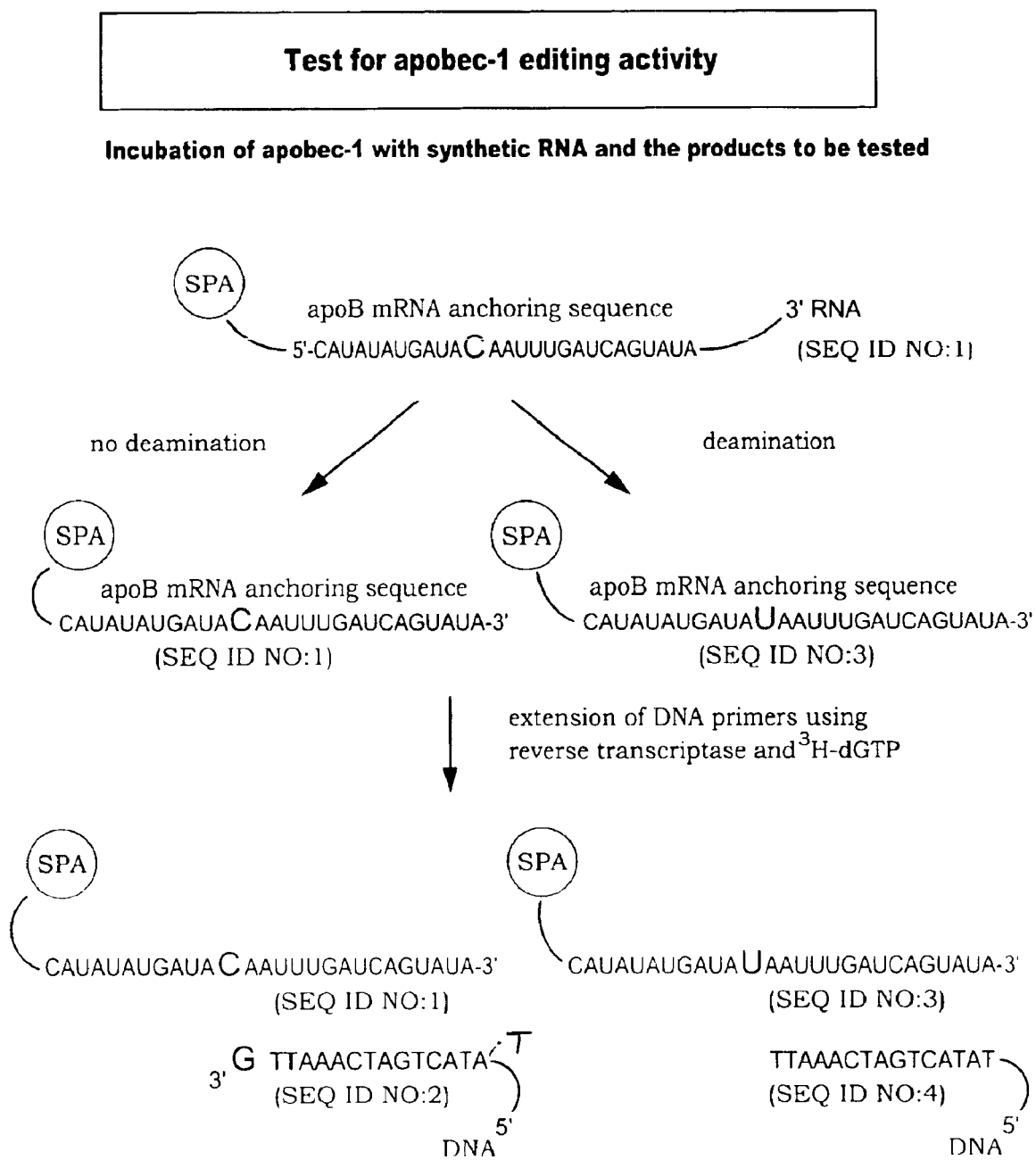
FIG. 4: Screening of inhibitors of apobec-1 deaminase activity using a technique for detecting deamination using the SPA® system. The technique uses a synthetic RNA sequence containing the anchoring sequence (about 50 nucleotides in the case of apobec-1) coupled to an SPA® bead. After incubating with the test inhibitors in the presence of the enzyme in the necessary medium, a complementary primer of the 3' sequence of the deaminated RNA site is added under hybridization conditions. Reverse transcriptase enzyme and radiolabelled nucleotides (only $d^3HGTP$ in the example shown) are then added. In the case of deamination, no incorporation takes place and the signal detected cannot be distinguished from background noise. In the case of the activity of the inhibitor (no deamination), the radiolabelled nucleotide is incorporated and a signal is detected.

Screening of Molecules Capable of Inhibiting Apobec-1 Deaminase Activity Using the SPA® System The example uses a synthetic RNA sequence containing the anchoring sequence of apobec-1 (about 50 nucleotides (Shah R R et al (1991), J. Biol. Chem., 16301–16304 and Davies M S et al (19891, J. Biol. Chem., 13395–13398) coupled to an SPA® bead (system sold by Amersham) disposed in a 96 well plate using the technique described in French patent application 97 04388. Briefly, after incubating with the test inhibitors in the presence of the enzyme in the medium and with the necessary reagents, a complementary primer of the 3' sequence of the deaminated RNA is added under hybridization conditions (Maniatis T et al., (1982), "Molecular Cloning, a Laboratory Manual" Cold Spring Harbor, NY). Reverse transcriptase enzyme and radiolabelled nucleotides (only $d^3$HGTP in the example shown in FIG. 4) are then added. In the present case, it would also be possible to use $d^3$HTTP. In the case of deamination, i.e., normal activity of the apobec-1 enzyme, no incorporation takes place and the signal detected, due to proximity scintillation of the SPA beads, cannot be distinguished from background noise. In the case of activity of the inhibitor, the apobec-1 deamination activity is reduced, rendering incorporation of a radiolabelled nucleotide possible (or two if $d^3$HTTP is also used) at the 3' end of a portion of the hybridized primers. In this case, a scintillation signal can be detected which can be distinguished from the background noise.

TABLE 1

| Disease | Phenotype | Diagnosis | Deficiency |
| --- | --- | --- | --- |
| Anderson's disease | Chronic diarrhoea Poor fat absorption Lack of vigour Retarded growth Moderate neurological symptoms | Low cholesterol and apoB100 level Normal triglyceride level apoB48 and chylomicrons absent after a fat-rich meal | ? |
| Abetalipo-proteinemia | Chronic diarrhoea Poor fat absorption Lack of energy Retarded growth Very severe neurological symptoms | Low cholesterol level, apoB100 and apoB48 absent Chylomicrons, VLDL, LDL absent Low triglyceride and cholesterol levels | MTP |
| Hypobetalipo-proteinemia | Indistinguishable from foregoing | Homozygotes have a low cholesterol and triglyceride level Heterozygotes have approximately 50% of cholesterol, triglyceride and apoB100 levels | Truncated apoB gene. |

What is claimed is:

1. A method of identifying a drug candidate for the treatment of obesity or other diseases characterized by hyperlipidemia or type II diabetes (non insulin dependent), comprising:
   a) incubating a synthetic RNA sequence comprising the anchoring sequence of apobec-1 with a test inhibitor and an apobec-1 enzyme;
   b) adding a complementary primer of 3' sequence of the synthetic sequence under hybridizing conditions;
   c) adding reverse transcriptase and a radiolabelled nucleotide; and
   d) detecting whether the inhibitor inhibits the apobec-1 enzyme by detecting the absence of deamination of the anchoring sequence, wherein inhibition of the apobec-1 enzyme is indicative that said test inhibitor is a drug candidate for the treatment of obesity or other diseases characterized by hyperlipidemia or type II diabetes (non insulin dependent).

2. A method according to claim 1, wherein the anchoring sequence has the sequence 5' CAUAUAUGAUACAAU-UUGAUCAGUAUA 3' (SEQ ID NO:1).

3. A method according to claim 2, wherein the anchoring sequence is coupled to a bead.

4. A method according to claim 1, wherein the complementary 3' primer has the following sequence 3' TTAAAC-TAGTCATAT 5' (SEQ ID NO: 4) or 3' GTTAAACTAGT-CATAT 5' (SEQ ID NO 2).

5. A method according to claim 1, wherein the radiolabelled nucleotide is $d^3HGTP$ or $d^3HGTP$ and $d^3HTTP$.

6. A method according to claim 1, wherein the absence of deamination of the anchoring sequence is detected by detecting the incorporation of the radiolabelled nucleotide into the primer.

7. A method of identifying a drug candidate for the treatment of obesity or other diseases characterized by hyperlipidemia or type II diabetes (non insulin dependent), comprising:
   a) providing a sample comprising a nucleic acid sequence encoding an apobec-1 enzyme or an ABBP-1 protein;
   b) contacting the sample with a test compound; and
   c) determining whether said test compound inhibits expression of said nucleic acid sequence encoding the apobec-1 enzyme or the ABBP-1 protein, wherein an inhibition of expression of said nucleic acid is indicative that said test compound is a drug candidate for the treatment of obesity or other diseases characterized by hyperlipidemia or type II diabetes (non insulin dependent).

8. A method according to claim 7, wherein the test compound is a single stranded antisense molecule comprising at least 12 nucleotides that can bind to the nucleic acid sequence encoding the apobec-1 enzyme.

9. A method of identifying an inhibitor of an apobec-1 enzyme wherein the method comprises:
   a) incubating a synthetic RNA sequence comprising an anchoring sequence of apobec-1 with a test inhibitor and the apobec-1 enzyme;
   b) adding a complementary primer of a 3' sequence of a synthetic sequence under hybridizing conditions;
   c) adding reverse transcriptase and a radiolabelled nucleotide; and,
   d) detecting the absence of deamination of the anchoring sequence of apobec-1, which is indicative that the test compound inhibits the apobec-1 enzyme.

10. A method for identifying an inhibitor of an apobec-1 enzyme activity wherein the method comprises:
   a) providing a sample comprising a nucleic acid sequence encoding the apobec-1 enzyme;
   b) contacting the sample with a test compound; and,
   c) determining whether said test compound inhibits expression of said nucleic acid sequence encoding the apobec-1 enzyme, wherein inhibition of the expression of said nucleic acid sequence is indicative that the test compound is an inhibitor of apobec-1 enzyme activity.

* * * * *

SEQUENCE LISTING

<160> NUMBER OF SEQ ID NOS: 4

<210> SEQ ID NO 1
<211> LENGTH: 27
<212> TYPE: RNA
<213> ORGANISM: Homo sapiens
<300> PUBLICATION INFORMATION:

-continued

```
<301> AUTHORS: Shah, RR., Knott, TJ., Legros, JE., Navaratnam, N., Greeve, JC.,
      Scott, J
<302> TITLE: Sequence Requirements for the Editing of Apolipoprotein B mRNA
<303> JOURNAL: Journal of Biological Chemistry
<304> VOLUME: 266
<305> ISSUE: 25
<306> PAGES: 16301-16304
<307> DATE: 1991-09-05
<308> DATABASE ACCESSION NUMBER: GenBank g4502152
<309> DATABASE ENTRY DATE: 1986-10-31
<300> PUBLICATION INFORMATION:
<301> AUTHORS: Davies, MS., Wallis, SC., Driscoll, DM., Wynne, JK., Williams, GW.,
      Powell, LM., Scott, J.
<302> TITLE: Sequence Requirements for Apolipoprotein B RNA Editing in Transfected
      Rat Hepatoma Cells
<303> JOURNAL: Journal of Biological Chemistry
<304> VOLUME: 264
<305> ISSUE: 23
<306> PAGES: 13395-13398
<307> DATE: 1989-08-15
<308> DATABASE ACCESSION NUMBER: GenBank g4502152
<309> DATABASE ENTRY DATE: 1986-10-31

<400> SEQUENCE: 1
cauauaugau acaauuugau caguaua                                        27

<210> SEQ ID NO 2
<211> LENGTH: 16
<212> TYPE: DNA
<213> ORGANISM: Homo sapiens

<400> SEQUENCE: 2
tatactgatc aaattg                                                    16

<210> SEQ ID NO 3
<211> LENGTH: 27
<212> TYPE: RNA
<213> ORGANISM: Homo sapiens

<400> SEQUENCE: 3
cauauaugau auaauuugau caguaua                                        27

<210> SEQ ID NO 4
<211> LENGTH: 15
<212> TYPE: DNA
<213> ORGANISM: Homo sapiens

<400> SEQUENCE: 4
tatactgatc aaatt                                                     15
```